United States Patent [19]
Davidson et al.

[11] Patent Number: 5,785,050
[45] Date of Patent: Jul. 28, 1998

[54] OXYGEN VALVE SYSTEM

[76] Inventors: Brian R. Davidson; Gilbert Davidson, both of 8132 Woodland Dr., Indianapolis, Ind. 46278

[21] Appl. No.: 811,244

[22] Filed: Mar. 3, 1997

[51] Int. Cl.⁶ .................................................. F16K 31/145
[52] U.S. Cl. .................. 128/205.24; 128/207.12; 128/207.16
[58] Field of Search .................... 128/205.24, 201.28, 128/203.11, 204.18, 204.28, 207.12, 207.16; 251/61, 61.2

[56] References Cited

U.S. PATENT DOCUMENTS

| | | | |
|---|---|---|---|
| 3,151,628 | 10/1964 | Heckert | 251/61 |
| 3,194,497 | 7/1965 | Thorburn | 251/61 |
| 3,688,794 | 9/1972 | Kowalski | 137/81 |
| 4,008,716 | 2/1977 | Amlong | 128/205.24 |
| 4,877,058 | 10/1989 | Stoll | 251/61 |

*Primary Examiner*—Aaron J. Lewis
*Assistant Examiner*—V. Srivastava
*Attorney, Agent, or Firm*—Daniel J. O'Connor

[57] ABSTRACT

An intermittent medical gas or oxygen delivery and regulator valve system which utilizes a single diaphragm and allows medical gas delivery through a central path in a valve stem. The valve may be easily retrofit to nearly all medical gas delivery systems currently in use and is thus expected to have widespread commercial appeal. The boundary between the valve stem and valve shuttle is of a novel design which results in a virtually frictionless movement by the shuttle element. The combination of elements results in a simplified and more efficient, long-life design.

1 Claim, 1 Drawing Sheet

OXYGEN VALVE SYSTEM

BACKGROUND OF THE INVENTION

1. Field of the Invention

The present invention generally concerns a medical gas valve used in systems for respiratory therapy of patients in a hospital, home or emergency environment.

Oxygen is the normal gas being utilized although other medical gas systems may benefit from the principles of the invention.

2. Description of the Prior Art

U.S. Pat. No. 4,054,133 shows a rather complex regulating system based upon patient need for oxygen. It includes a multiple valving design which has apparently never been mass-produced or sold.

U.S. Pat. No. 5,360,000 discusses the above prior art and describes the need for a simplified low-cost oxygen demand valve for widespread usage and to avoid waste of oxygen.

However, U.S. Pat. No. 5,360,000 requires multiple diaphragms in its design and would thus be relatively expensive to manufacture. It would also be subject to the normal wear and operational problems of diaphragm valves.

Accordingly, it is an object of the present invention to set forth a novel demand-type medical gas valve of a simplified design which may be readily mass-produced and sold.

It is a further object of the invention to describe a medical gas control valve of a modular design which may be easily used in most existing oxygen systems.

It is a still further object to show a novel diaphragm valve which is less subject to wear than valves heretofore known in the art.

It is a further object of the invention to demonstrate a demand-type valve which operates in a virtually frictionless manner for enhanced performance and longer life.

These and other objects and advantages of the present invention will be apparent to those of skill in the art from the description which follows.

SUMMARY OF THE INVENTION

The FLOTEC OXYSAVRR™ is an intermittent flow device suitable for use in controlling the flow of medical gases to patients. It is a pilot-operated two position, two-way valve and may be biased to be normally open or normally closed.

The operator is a diaphragm which is attached to the valve shuttle. The diaphragm is acted upon by the slight vacuum produced by the user's inhalation during the respiratory cycle. The positive pressure produced by exhalation acts on the diaphragm, moving the valve shuttle to the closed position.

The valve is unique in that flow is conducted through a tube, the stem, which is blocked at the midpoint. A set of orifices on each side of the central inner wall allows gas to exit the stem, flow around the obstruction and reenter the stem on the other side of the obstruction. The gas flows through the center of the diaphragm.

The shuttle which encircles the stem contains a cavity which connects the two sets of orifices when inhalation occurs. Exhalation causes the diaphragm to move the shuttle to the closed position, shutting off flow.

Unlike other designs using two or more diaphragms, there are no unbalanced forces acting within the valve. The shuttle moves freely and floats on a thin layer of gas. The stem has a number of concentric grooves on the outer surface thereof.

Each of these grooves acts as an obstruction to flow of the fluid between the surfaces of the shuttle and the stem. The grooves also act to center the shuttle on the stem. When pressurized, there is no metal-to-metal contact between the shuttle and the stem. The thin layer of gas acts as a hydrodynamic bearing so that the mechanism is almost frictionless.

The stem and shuttle are hard-coated, a process in which the surface of each is electrochemically converted to aluminum oxide or equivalent, an extremely hard, inert material which is also very slippery.

The valve can be equipped with biasing springs which move the shuttle to the open or closed position when the device is not in operation.

The OXYSAVRR module is designed to be inserted between a pressure reducing section and a flow meter module as a regulator.

The OXYSAVRR™ contains a port which allows negative or positive pilot pressure to be admitted into the housing where it acts upon the diaphragm causing the shuttle to move.

A double lumen hose and cannula provides conductors for both the pilot pressure and the flow of gas to the user.

DESCRIPTION OF THE DRAWING FIGURES

Figure 3:
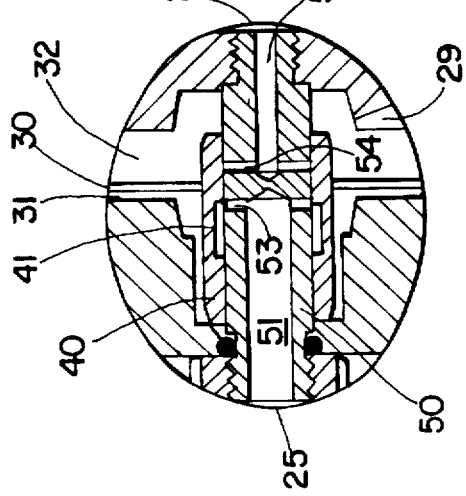

FIG. 3 also shows an enlarged view of the stem and shuttle in a valve closed position with the diaphragm moved to the left.

Figure 4:
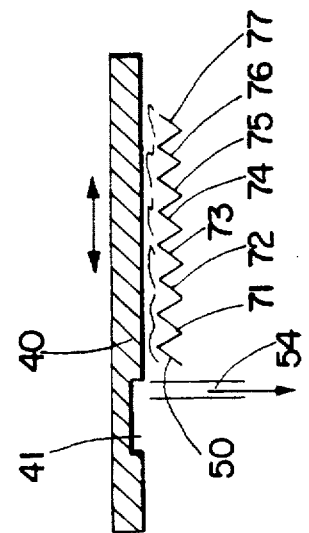

FIG. 4 shows an enlarged schematic view of the boundary between the movable shuttle 40 and the fixed stem 50 and illustrates the frictionless movement created by the present invention.

DESCRIPTION OF THE PREFERRED EMBODIMENT

Figure 1:
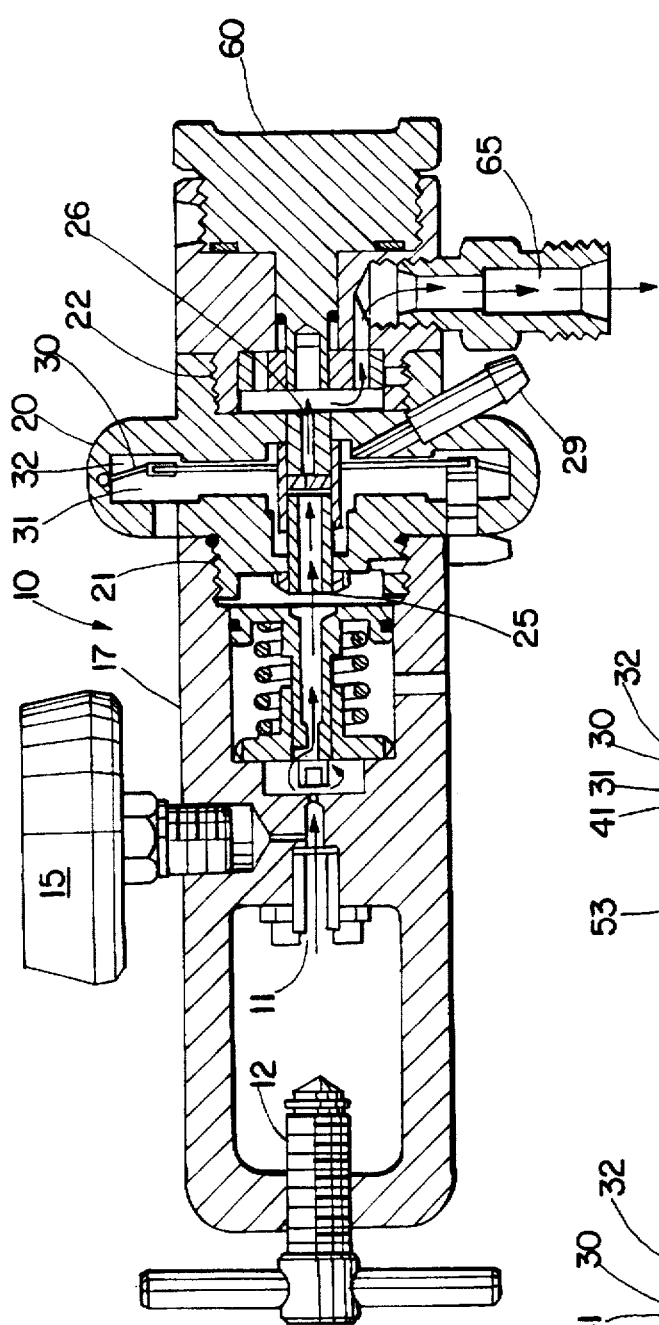
FIG. 1 shows a lateral sectional view of the system and illustrates most of the major components and the flow in a valve open position.
Figure 2:
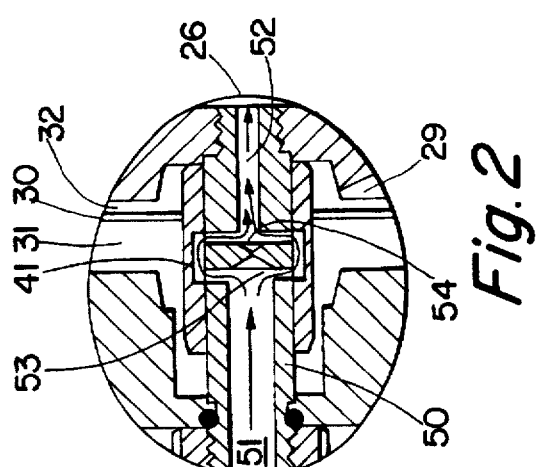
FIG. 2 shows an enlarged view of the stem and shuttle and illustrates the flow path in a valve open position.

Referring to the FIGS. 1, 2, and 3, the valve 20 of the invention is shown as installed between a pressure reducing section 17 and a flow meter module 60. Threads 21 and 22 of valve 20 allow a modular installation of the unit for ease of use in virtually any system.

A typical system could include a locking device 12 and a pressure gauge 15.

A supply of oxygen enters the system at 11 and passes through the pressure reducing section 17 to the entry port 25 of valve 20.

Entry port 25 is part of a stem 50. See FIGS. 2 and 3.

The stem 50 has passages 51 and 52 formed therein. It also has orifices 53 and 54 and is blocked at the midpoint.

As shown in the enlarged view of FIG. 2, a movable shuttle 40 encircles the stem 50 and has a diaphragm 30 attached thereto.

The shuttle 40 has a cavity 41 therein which connects the orifices 53 and 54 when inhalation occurs, i.e. when the diaphragm 30 is in the right position of FIG. 2.

Thus, in the valve open position of FIG. 2, the gas is allowed to flow through the shuttle 40 into passage 52 and out the exit port 26. From there, it passes through the flow meter module and passage 65 to the patient via a cannula (not shown). Note numeral 65 in FIG. 1.

The position of diaphragm 30 and hence shuttle 40 are controlled via port 29 which allows negative or positive pressure to be admitted into the housing depending upon whether the patient is inhaling or exhaling.

Port 29 would be connected via another line of the cannula to the patient and be responsive to patient breathing.

When the patient exhales, the diaphragm 30 and shuttle 40 are moved to the left valve closed position of FIG. 3. As shown in FIG. 3, cavity 41 does not allow gas flow and thus no oxygen is supplied through the valve.

The central flow through the surrounding diaphragm 30 means that the diaphragm is not constantly abutting a port as in prior art designs. Thus, wear is greatly reduced and valve life and operation are enhanced.

The present system also eliminates the need for a second actuating diaphragm thus simplifying the overall design.

Diaphragm 30 is attached to valve housing 20 and to the shuttle 40 and simply moves back and forth to change the size of chambers 31 and 32.

Another important aspect of the invention concerns the nearly frictionless movement of the shuttle 40.

As shown in FIG. 4, the outer surface of stem 50 is machined to form a series of concentric grooves.

Such grooved configuration allows a small amount of the medical gas such as oxygen to flow between the stem 50 and the shuttle 40. For example, as oxygen enters at groove 71 it is at a certain elevated pressure P1. As it flows through and over the succeeding grooves 72–77, a damming and pressure reducing effect is created so that it is at a lower pressure P2 at groove 77.

Such pressure drop means there is virtually no gas leakage and, importantly, that the shuttle 40 floats back and forth on a hydrodynamic cushion of oxygen.

Such gas cushion serves to center the shuttle in relation to the stem and results in a nearly frictionless movement between the shuttle 40 and stem 50.

The groove dimensions may vary depending upon the particular results desired.

Thus, even when the shuttle 40 is in the valve closed and gas blocking position, small amounts of the gas from orifices 54 leak into the grooved areas 71–77 to continue to provide a frictionless and hydrodynamic bearing.

In practice, the concentric grooves 71–77 would be placed along all surfaces of stem 50 which could contact the shuttle 40. A frictionless flow is thus created all along the surface of stem 50.

In practice of the invention, a biasing spring (not shown) may be added to urge the shuttle and diaphragm into a normally open or normally closed position depending upon particular patient treatment needs.

It will thus be appreciated that a long-life and easily installed gas regulator system has been described and shown. The central flow path and frictionless flow design allow a single diaphragm to be utilized while simultaneously enhancing system performance and operation.

While described in relation to a medical gas system, the principles set forth herein have wide-ranging applicability to other types of fluid flow and regulator valve systems. It is anticipated that further patentable uses and applications will be filed with the U.S. Patent Office.

We claim:

1. A medical gas delivery system comprising:

means for reducing pressure (17) of said medical gas, regulator valve means (20) for controlling said medical gas, flow meter module means (60) for supplying said medical gas to a patient, wherein said regulator valve means (20) comprises single diaphragm means (30) for moving a shuttle (40), a central stationary stem means (50) for admitting flow of said medical gas and for discharging said medical gas, wherein said shuttle means is movable along said stem means, wherein said regulator valve (20) includes a port means (29) for responding to the inhalation and exhalation of a patient, wherein said stem means (50) includes concentric groove means (71) for providing a frictionless movement between said stem and said shuttle, wherein said stem means (50) includes orifice means (53,54) for supplying said medical gas to the region of said shuttle means, wherein said stationary stem means has a midpoint obstruction therein, wherein said shuttle means includes a cavity means (41) for enabling gas flow around said stem midpoint obstruction, wherein said shuttle means (40) is affixed directly to said diaphragm means (30) for movement therewith, wherein said orifice means (53,54) provide a central flow path for medical gas to flow through the center of said diaphragm.

* * * * *